(12) United States Patent
Nunome

(10) Patent No.: US 6,315,734 B1
(45) Date of Patent: Nov. 13, 2001

(54) PULSE-WAVE PROPAGATION INFORMATION OBTAINING APPARATUS

(75) Inventor: Tomohiro Nunome, Komaki (JP)

(73) Assignee: Colin Corporation, Komaki (JP)

(*) Notice: Subject to any disclaimer, the term of this patent is extended or adjusted under 35 U.S.C. 154(b) by 0 days.

(21) Appl. No.: 09/494,038

(22) Filed: Jan. 31, 2000

(30) Foreign Application Priority Data

Nov. 1, 1999 (JP) .................................................. 11-310655

(51) Int. Cl.[7] ...................................................... A61B 5/02
(52) U.S. Cl. ........................... 600/500; 600/490; 600/494
(58) Field of Search ..................................... 600/500, 501, 600/502, 503, 481, 483, 484, 485, 486, 490, 492, 493, 494, 495, 496

(56) References Cited

U.S. PATENT DOCUMENTS

| | | |
|---|---|---|
| 4,446,872 | 5/1984 | Marsoner et al. . |
| 5,755,669 * | 5/1998 | Ono et al. ............................. 600/494 |
| 5,803,911 * | 9/1998 | Inukai et al. .......................... 600/387 |
| 5,921,936 * | 7/1999 | Inukai et al. .......................... 600/490 |
| 6,027,453 * | 2/2000 | Miwa et al. ........................... 600/485 |
| 6,036,651 * | 3/2000 | Inukai et al. .......................... 600/485 |
| 6,120,456 * | 9/2000 | Oka et al. .............................. 600/485 |

FOREIGN PATENT DOCUMENTS

| | | |
|---|---|---|
| 0 420 085 A2 | 4/1991 | (EP) . |
| 0 716 829 A2 | 6/1996 | (EP) . |
| 0 898 938 A2 | 3/1999 | (EP) . |
| 10-146322 | 6/1998 | (JP) . |
| WO 97/48332 | 12/1997 | (WO) . |

* cited by examiner

*Primary Examiner*—John P. Lacyk
*Assistant Examiner*—Navin Natnithithadha
(74) *Attorney, Agent, or Firm*—Oliff & Berridge, PLC (57) ABSTRACT

An apparatus for obtaining an information relating to a propagation velocity of a pulse wave which propagates through an artery of a living subject, including: a first signal detecting device which is adapted to be worn on a first portion of the subject and which detects a first signal generated from the first portion in synchronism with a heart beat of the subject; a pulse-wave detecting device which is adapted to be worn on a second portion of the subject and which detects, as a second signal, a notch of the pulse wave generated from the second portion in synchronism with the heart beat of the subject; a pressing device which is adapted to be worn on a third portion of the subject to press the third portion, the third portion being on a downstream side relative to the second portion with respect to the artery and being in proximity to the second portion; and pulse-wave propagation time determining means for determining, as the information, a time difference between a time when the first signal is detected by the first signal detecting device and a time when the notch of the pulse wave is detected by the pulse-wave detecting device in a state in which the third portion is pressed by the pressing device.

9 Claims, 7 Drawing Sheets

FIG. 5A $P_{1M}$=0mmHg

FIG. 5B $P_{1M}$=60mmHg

FIG. 5C $P_{1M}$=170mmHg

FIG. 5D $P_{1M}$=230mmHg

PULSE-WAVE PROPAGATION INFORMATION OBTAINING APPARATUS

BACKGROUND OF THE INVENTION

1. Field of the Invention

The present invention relates to an apparatus for obtaining an information relating to a propagation velocity of a pulse wave which propagates through an artery of a living subject, for example, a pulse-wave propagation time or a pulse-wave propagation velocity.

2. Related Art Statement

There have been proposed various pulse-wave propagation information obtaining apparatuses for obtaining an information relating to a propagation velocity of a pulse wave which propagates through an artery of a living subject. The pulse-wave propagation information is used for estimating a blood pressure, a degree of an arterial sclerosis, or a peripheral resistance of the subject, or the like.

The pulse-wave propagation information includes a pulse-wave propagation velocity and/or a pulse-wave propagation time. Since the pulse-wave propagation velocity is determined by dividing a propagation path (distance) through which the pulse wave propagates by the pulse-wave propagation time, it is needed to determine the pulse-wave propagation time. The pulse-wave propagation time is determined as follows: First, a first and a second signal detecting device are worn on a first and a second portion of the subject, respectively, and detect a first signal produced in synchronism with a heart beat of the subject and a second signal produced in synchronism with the heart beat of the subject, respectively. Then, a time difference between a time when the first signal is detected and a time when the second signal is detected is determined. The time difference is defined as the pulse-wave propagation time.

For example, a phonocardiographic transducer worn on a chest of the subject is employed as the first signal detecting device, and a second heart sound II detected by the phonocardiographic transducer is employed as the first signal. A carotid pulse sensor worn on a cervix of the subject is employed as the second signal detecting device, and a notch of a carotid pulse wave detected in synchronism with the detected second heart II by the carotid pulse sensor is employed as the second signal. The notch of the carotid pulse wave is defined as a point at which the amplitude of the carotid pulse wave (i.e., the intensity of the second signal) starts increasing after decreasing from the maximum amplitude of the carotid pulse wave. A time difference between a time when the second heart sound II is detected and a time when the notch of the carotid pulse wave is detected is determined as the pulse-wave propagation time. It is generally understood that the pulse-wave propagation time determined based on the second heart sound II and the notch of the carotid pulse wave is suitable for evaluating a pulse-wave propagation time of a central portion of the subject. The carotid pulse sensor for detecting the carotid pulse wave is disclosed in Laid-Open Publication No. 10-146322 of unexamined Japanese Patent Application.

However, it needs a great skill to wear the carotid pulse sensor on an appropriate portion of the cervix of the subject. If the carotid pulse sensor is not worn on the appropriate portion of the cervix of the subject, an accurate carotid pulse wave may not be detected, so that an incorrect notch of the carotid pulse wave may be detected. Therefore, an accurate pulse-wave propagation time may not be determined.

Moreover, in the case where a pulse-wave detecting device worn on a different portion of the subject than the cervix is employed in place of the carotid pulse sensor, a notch of the detected pulse wave may be employed as the second signal. However, if the notch of the pulse wave is obscure, a time when the notch is detected can not be determined accurately. Therefore, an accurate pulse-wave propagation time can not be determined.

SUMMARY OF THE INVENTION

It is therefore an object of the present invention to provide a pulse-wave propagation information obtaining apparatus which can obtain an accurate information relating to a propagation velocity of a pulse wave which propagates through an artery of a living subject.

The above object has been achieved by the present invention, which provides an apparatus for obtaining an information relating to a propagation velocity of a pulse wave which propagates through an artery of a living subject, comprising: (a) a first signal detecting device which is adapted to be worn on a first portion of the subject and which detects a first signal generated from the first portion in synchronism with a heart beat of the subject; (b) a pulse-wave detecting device which is adapted to be worn on a second portion of the subject and which detects, as a second signal, a notch of the pulse wave generated from the second portion in synchronism with the heart beat of the subject; (c) a pressing device which is adapted to be worn on a third portion of the subject to press the third portion, the third portion being on a downstream side relative to the second portion of the subject with respect to the artery and being in proximity to the second portion; and (d) pulse-wave propagation time determining means for determining, as the information, a time difference between a time when the first signal is detected by the first signal detecting device and a time when the notch of the pulse wave is detected by the pulse-wave detecting device in a state in which the third portion of the subject is pressed by the pressing device.

In the apparatus in accordance with the present invention, the pulse-wave propagation time determining means determines, as a pulse-wave propagation time, the time difference between the time when the first signal is detected by the first signal detecting device and the time when the notch of the pulse wave is detected by the pulse-wave detecting device in the state in which an artery of the subject under the pressing device is pressed by the pressing device. The pulse-wave detecting device is worn on the portion of the subject being on an upstream side relative to the pressing device with respect to the artery and being in proximity to the pressing device. In the state in which the artery is pressed by the pressing device, a notch of the pulse wave can be clearly detected by the pulse-wave detecting device located upstream of, and near to, the pressing device. Therefore, the time when the notch of the pulse wave is detected is accurately determined. Thus, the apparatus according to the present invention can accurately determine a pulse-wave propagation time based on the accurate time when the notch of the pulse wave is detected.

According to a preferred feature of the present invention, the pulse-wave detecting device comprises a brachial pulse-wave detecting device which is adapted to be worn on an upper arm of the subject and which detects a notch of a brachial pulse wave of the subject, and the pressing device comprises a first rubber bag which is adapted to be worn on the upper arm of the subject for determining a blood pressure of the subject, the apparatus further comprising: a pressure control device which changes a pressing pressure of the first rubber bag; and a blood pressure determining device which determines the blood pressure of the subject, based on signals successively detected while the pressing pressure of the first rubber bag is changed by the pressure control device. In this case, the pulse-wave propagation information obtaining apparatus can determine the blood pressure of the subject in addition to the information relating to the propagation velocity of the pulse wave.

According to another feature of the present invention, the brachial pulse-wave detecting device comprises a second rubber bag for detecting the brachial pulse wave of the subject, the second rubber bag is adapted to be worn on an upstream side relative to a portion of the upper arm on which the first rubber bag is worn, and the apparatus further comprises an outer bag in which the first and second rubber bags are accommodated in a state in which the first and second rubber bags are spaced from each other. Thus, since only the outer bag and the first signal detecting device are worn on the respective portions of the subject, the present apparatus can easily obtain the information relating to the propagation velocity of the pulse wave.

According to another feature of the present invention, the pulse-wave propagation time determining means determines the time difference between the time when the first signal is detected and the time when the notch of the brachial pulse wave is detected by the brachial pulse-wave detecting device in the state in which the upper arm is pressed by the first rubber bag with a pressing pressure greater than a reference value which is greater than a systolic blood pressure of the subject, and the blood pressure determining device determines, after detection of the first signal and the notch of the brachial pulse wave, the blood pressure of the subject, based on the signals successively detected while the pressing pressure of the first rubber bag is decreased by the pressure control device. In the apparatus, in a state in which the pressing pressure of the first rubber bag is increased to a value not lower than the reference value for determining the blood pressure of the subject, the first signal and the notch of the brachial pulse wave are detected. Thus, the present apparatus can obtain the blood pressure of the subject and the pulse-wave propagation time at one time.

According to another feature of the present invention, the pulse-wave propagation time determining means determines the time difference between the time when the first signal is detected and the time when the notch of the pulse wave is detected in the state in which the third portion is pressed by the pressing device with a pressing pressure greater than a systolic blood pressure of the subject. Thus, the pulse-wave propagation time determining means determines the time difference between the time when the first signal is detected and the time when the notch of the pulse wave is detected in a state in which a blood flow in the artery under the pressing device is completely stopped on the downstream side relative to the pulse-wave detecting device with respect to the artery. In the state in which the blood flow in the artery on the downstream side relative to the pulse-wave detecting device is completely stopped, the amplitude of the pulse wave detected by the pulse-wave detecting device significantly increases, so that the notch of the detected pulse wave can be clearly detected. Thus, the time when the notch of the pulse wave is detected is accurately determined, whereby the pulse-wave propagation time can be accurately determined.

According to another feature of the present invention, the first signal detecting device comprises a phonocardiographic transducer which detects, as the first signal, one of a first and a second heart sound of the subject.

According to another feature of the present invention, the phonocardiographic transducer has a switch which is manually operable for starting the apparatus.

According to another feature of the present invention, the apparatus further comprises a pulse-wave propagation velocity determining means for determining the propagation velocity of the pulse wave, by dividing a distance between a heart of the subject and the second portion of the subject by the time difference determined by the pulse-wave propagation time determining means.

According to another feature of the present invention, the apparatus further comprises an input device which is operable for inputting a stature of the subject, and the pulse-wave propagation velocity determining means comprises means for determining the distance between the heart of the subject and the second portion of the subject, based on the stature of the subject input through the input device, according to a predetermined relationship between distance and stature, and means for determining the propagation velocity of the pulse wave by dividing the determined distance by the time difference determined by the pulse-wave propagation time determining means.

BRIEF DESCRIPTION OF THE DRAWINGS

The above and optional objects, features and advantages of the present invention will be better understood by reading the following detailed description of the preferred embodiment of the invention when considered in conjunction with the accompanying drawings, in which.

DETAILED DESCRIPTION OF THE PREFERRED EMBODIMENT

Hereinafter, there will be described a pulse-wave propagation information (PWPI) obtaining apparatus 10 to which the present invention is applied, by reference to the drawings.

Figure 1:
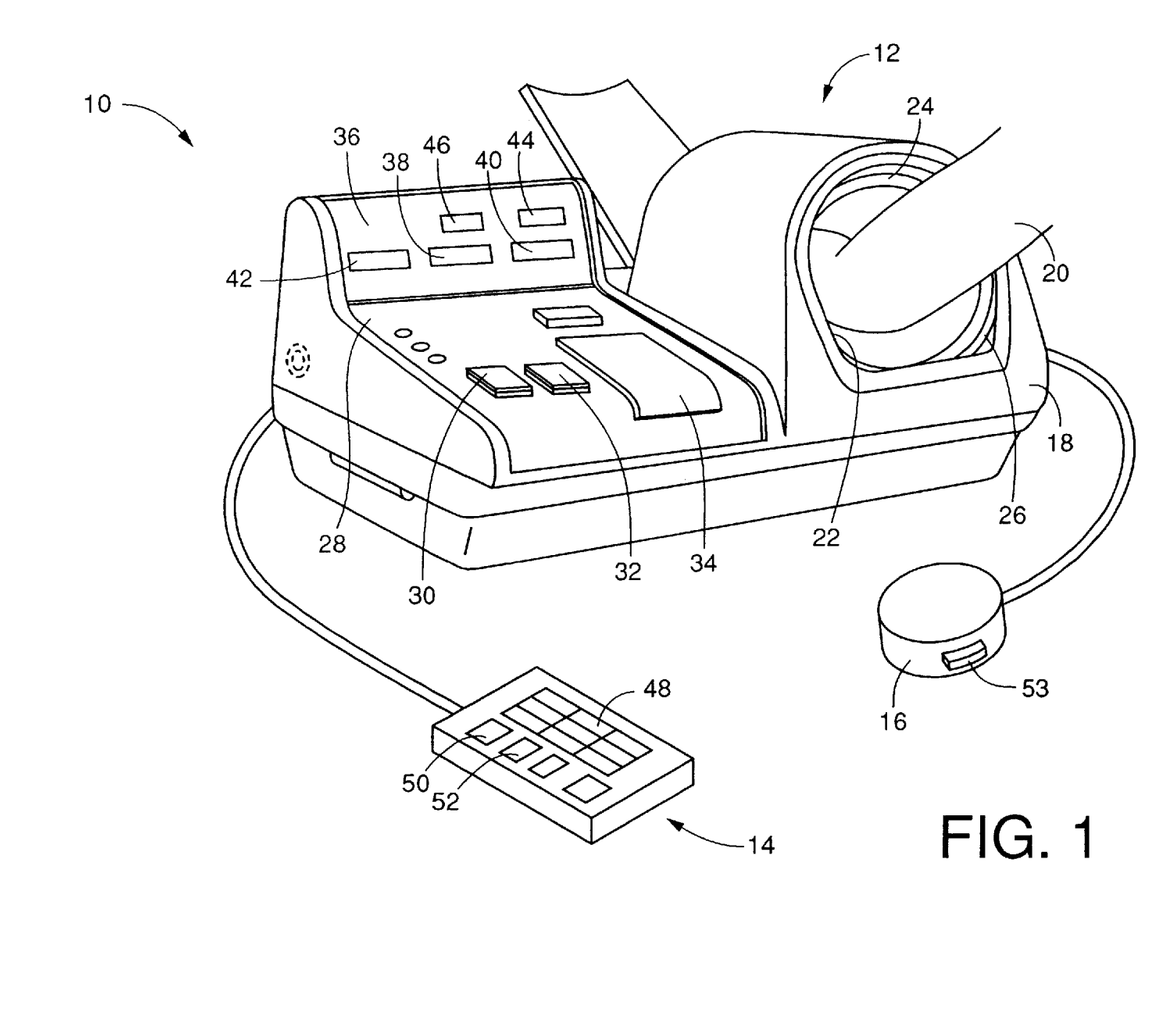
FIG. 1 is a perspective view of a pulse-wave propagation information obtaining apparatus including an automatic blood-pressure measurement function to which the present invention is applied.

FIG. 1 is a perspective view of the PWPI obtaining apparatus 10 including an automatic blood-pressure measurement function. As shown in FIG. 1, the PWPI obtaining apparatus 10 includes a main body 12, an input device 14 which is connected to the main body 12, and a phonocardiographic transducer 16 as a first signal detecting device. The phonocardiographic transducer 16 is supported by, for example, a left hand of a living subject such that the transducer 16 is worn on the chest of the subject and directed toward the heart of the subject.

The main body 12 of the apparatus 10 includes a housing 18 which includes a cylindrical arm receiver 22 into which an arm 20 of the subject is inserted, an operation panel 28, and a display panel 36. A flexible outer belt 26 having a relatively high rigidity is attached to an inner surface of the cylindrical arm receiver 22. The outer belt 26 has a cuff 24 on its inner surface which faces the inserted arm 20. In the operation panel 28, a start switch 30, a stop switch 32, and a printer 34, etc., are provided. In the display panel 36, a systolic blood-pressure (BP) display device 38, a diastolic blood-pressure (BP) display device 40, a pulse-wave propagation velocity (PWV) display device 42, a heart rate display device 44, and a time display device 46 are provided.

The input device 14 includes numeral keys 48 for inputting a stature and a weight of the subject, etc., a stature display device 50 for displaying the input stature, and a weight display device 52 for displaying the input weight. The phonocardiographic transducer 16 may be a known one, for example, an air-conduction-type one. The phonocardiographic transducer 16 is worn on the skin of chest of the subject with one of the left and right hands of the subject which is not inserted into the arm receiver 22, an adhesive tape, or the like. The phonocardiographic transducer 16 has a start switch 53 which is manually operable by the one hand of the subject, for starting the operation of the apparatus 10.

Figure 2:
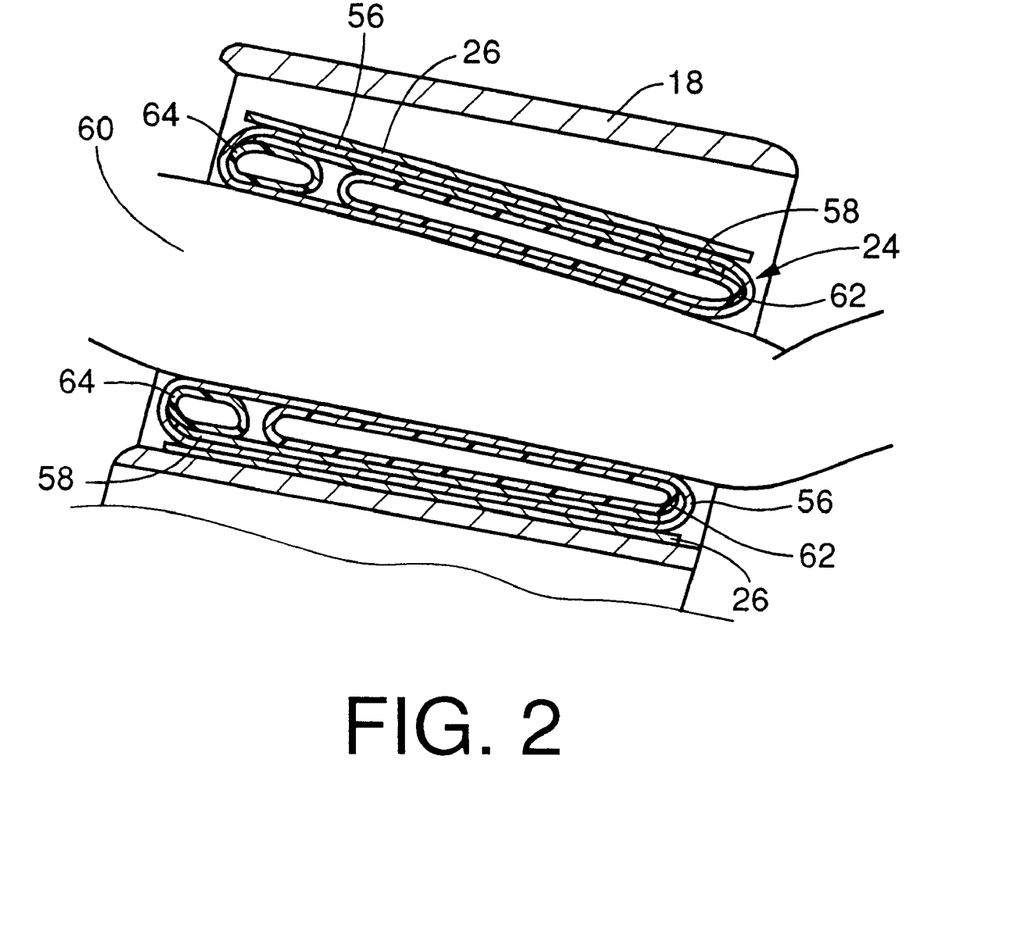
FIG. 2 is a cross sectional view of a cuff provided in a main body of the apparatus of FIG. 1, taken along a vertical plane parallel to a widthwise direction of the cuff.

FIG. 2 is a cross sectional view of the cuff 24, taken along a vertical plane parallel to a widthwise direction of the cuff 24. The cuff 24 is used for pressing a brachial artery in an upper arm 60 of the subject. As shown in FIG. 2, an outer bag 56 is attached to the inner surface of the outer belt 26. The outer bag 56 is formed of a cloth or a soft resin sheet. In the outer bag 56, a flexible inner belt 58 having a relatively high rigidity is provided. The outer bag 56 is biased by an elastic restoring force of the inner belt 58 in a direction in which the radius of the outer bag 56 increases. In addition, a first rubber bag 62 and a second rubber bag 64 are fixed to an inner surface of the inner belt 58 such that the second rubber bag 64 is spaced, by a small distance (e.g., about 1 cm), from the first rubber bag 62, on an upstream side relative to the first rubber bag 62 with respect to the brachial artery of the subject. The first rubber bag 62 has a first width (e.g., about 13 cm) suitable for pressing the brachial artery in the upper arm 60 to determine a blood pressure of the subject. The second rubber bag 64 is used for pressing the brachial artery in the upper arm 60 on the upstream side relative to the first rubber bag 62, and has a second width (e.g., about 3 cm) smaller than the first width of the first rubber bag 62. In the present embodiment, the first rubber bag 62 functions as a pressing device used when the blood pressure of the subject is determined. The first and second rubber bags 62, 64 are fixed to the inner surface of the inner belt 58, in the state in which the two bags 62, 64 are spaced from each other.

Figure 3:
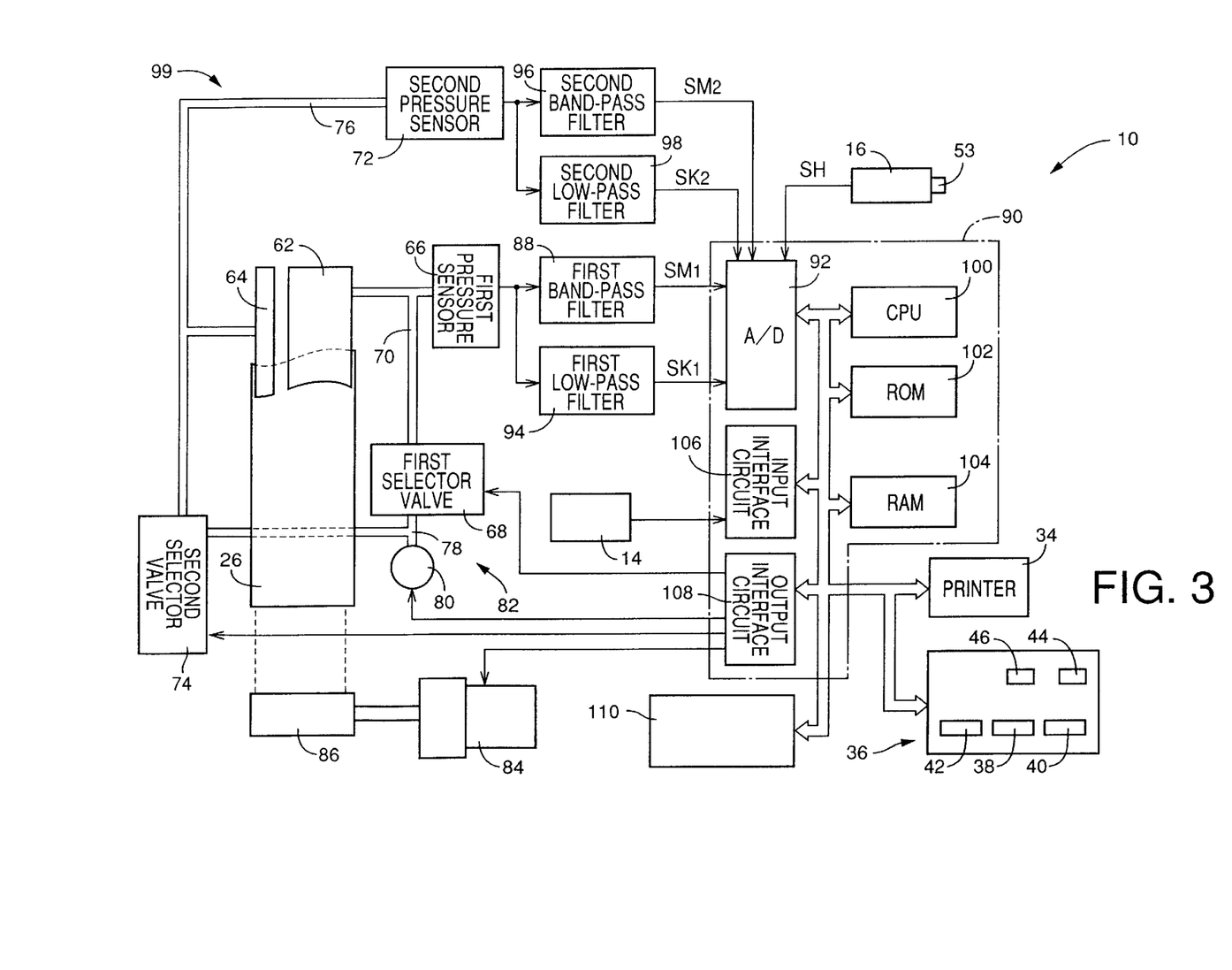
FIG. 3 is a block diagram for illustrating a circuit system of the apparatus of FIG. 1.

FIG. 3 is a block diagram for illustrating a circuit system of the PWPI obtaining apparatus 10. In the figure, the first rubber bag 62 is connected to a first pressure sensor 66 and a first selector valve 68 via a piping 70. The second rubber bag 64 is connected to a second pressure sensor 72 and a second selector valve 74 via a piping 76. The first and second selector valves 68, 74 are connected to an air pump 80 via a piping 78. The first selector valve 68 is selectively placed in an inflation position in which the first selector valve 68 permits a pressurized air to be supplied from the air pump 80 to the first rubber bag 62, a slow-deflation position in which the valve 68 permits the pressurized air to be slowly discharged from the bag 62, a quick-deflation position in which the valve 68 permits the pressurized air to be quickly discharged from the bag 62, and a pressure-hold position in which the valve 68 holds the pressure in the bag 62. Thus, the first selector valve 68, the piping 78 and the air pump 80 cooperate with each other to provide a pressure control device 82 which changes a pressing pressure of the first rubber bag 62. On the other hand, the second selector valve 74 is selectively placed in an inflation position in which the second selector valve 74 permits a pressurized air to be supplied to be supplied to the second rubber bag 64, a deflation position in which the valve 74 permits the pressurized air to be discharged from the bag 64, and a pressure-hold position in which the valve 68 holds the pressure in the bag 64.

The outer belt 26 supporting, on its inner surface, the cuff 24 which includes the first and second rubber bags 62, 64, is tighten by a drum 86 to which one end of the outer belt 26 is fixed and which is driven by a direct current (DC) motor 84 with reduction gears. The other end of the outer belt 26 is fixed to the housing 18. The first pressure sensor 66 detects an air pressure in the first rubber bag 62 and outputs an output signal $SP_1$ representative of the detected pressure of the first rubber bag 62. The output signal $SP_1$ is supplied to a first band-pass filter 88 and a first low-pass filter 94. The first band-pass filter 88 extracts, from the output signal $SP_1$, a first pulse-wave signal $SM_1$ representative of a pressure signal generated from the first rubber bag 62 in synchronism with a pulse of the subject. The first low-pass filter 94 extracts, from the output signal $SP_1$, a first rubber-bag pressure signal $SK_1$ representative of a static pressure of the first rubber bag 62. The first pulse-wave signal $SM_1$ and the first rubber-bag pressure signal $SK_1$ are supplied to an arithmetic control circuit 90 via an analog-to-digital (A/D) converter 92.

On the other hand, the second pressure sensor 72 detects an air pressure in the second rubber bag 64 and outputs an output signal $SP_2$ representative of the detected pressure of the second rubber bag 64. The output signal $SP_2$ is supplied to a second band-pass filter 96 and a second low-pass filter 98. The second band-pass filter 96 extracts, from the output signal $SP_2$, a second pulse-wave signal (i.e., brachial pulse-wave signal) $SM_2$ representative of a pressure signal generated from the second rubber bag 64 in synchronism with a pulse of the brachial artery of the subject. The second low-pass filter 98 extracts, from the output signal, $SP_2$, a second rubber-bag pressure signal $SK_2$ representative of a static pressure of the second rubber bag 64. The second pulse-wave signal $SM_2$ and the second rubber-bag pressure signal $SK_2$ are supplied to the arithmetic control circuit 90 via the A/D converter 92. In the present embodiment, the second rubber bag 64, the second pressure sensor 72 and the second low-pass filter 98 cooperate with each other to provide a brachial pulse-wave detecting device 99.

The arithmetic control circuit 90 is provided by a microcomputer including a central processing unit (CPU) 100, a read only memory (ROM) 102, a random access memory (RAM) 104, an input interface circuit 106, and an output interface circuit 108. The CPU 100 processes input signals according to control programs pre-stored in the ROM 102 by utilizing a temporary-storage function of the RAM 104, and outputs drive signals, display signals, and the like. More specifically, the CPU 100 determines blood pressure values BP and a pulse-wave propagation velocity PWV of the subject, based on a heart-sound signal SH supplied from the phonocardiographic transducer 16, the first pulse-wave signal $SM_1$ supplied from the first band-pass filter 88, the first rubber-bag pressure signal $SK_1$ supplied from the first low-pass filter 94, the second pulse-wave signal $SM_2$ supplied from the second band-pass filter 96, and the second rubber-bag pressure signal $SK_2$ supplied from the second low-pass filter 96, while the DC motor 84, the air pump 80, and the first and second selector valves 68, 74 are controlled according to the pre-stored programs. Then, the CPU 100 supplies the respective display signals to the systolic BP display device 38, the diastolic BP display device 40, and the PWV display device 42 so that the determined blood pressure values BP and pulse-wave propagation velocity PWV are respectively displayed. In addition, the determined BP and PWV are stored in a relevant portion of a storage device 110. The storage device 110 is provided by a known memory such as a magnetic disk, a magnetic tape, a volatile semiconductor memory, a nonvolatile semiconductor memory, or the like.

Figure 4:
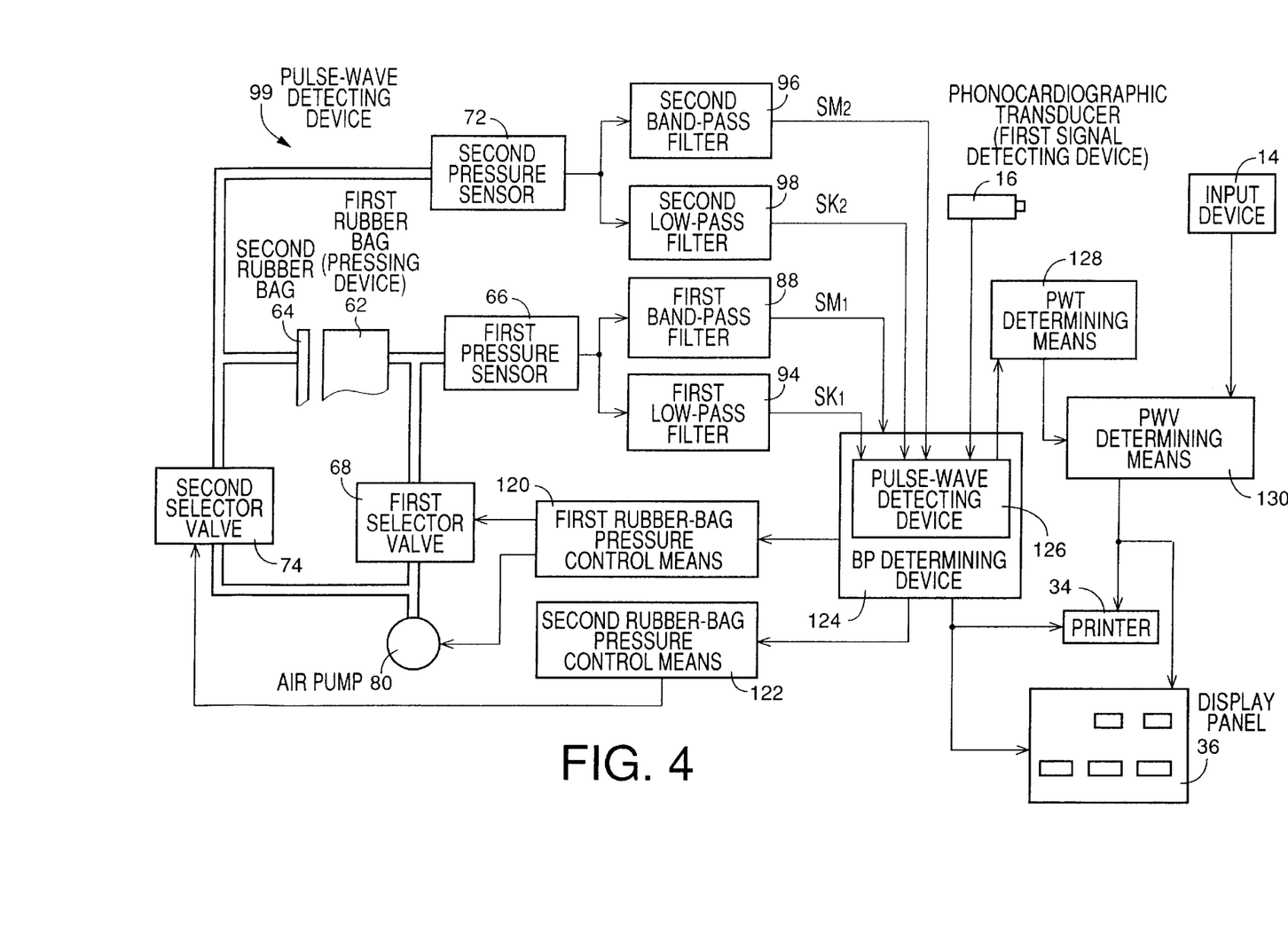
FIG. 4 is a block diagram for illustrating essential functions of an arithmetic control circuit of the apparatus of FIG. 1.

FIG. 4 is a block diagram for illustrating essential functions of the arithmetic control circuit 90 of the PWPI obtaining apparatus 10. In FIG. 4, a first rubber-bag pressure control means 120 controls the first selector valve 68 and the air pump 80 to control a pressing pressure of the first rubber bag 62. A second rubber-bag pressure control means 122 controls the second selector valve 74 to control a pressing pressure of the second rubber bag 64.

A blood-pressure (BP) determining device 124 includes a pulse-wave detecting device 126 which detects a pulse wave of the subject for determining a pulse-wave propagation time DT. The pulse-wave detecting device 126 monitors a first rubber-bag pressure $P_1$ of the first rubber bag 62, based on the first rubber-bag pressure signal $SK_1$ supplied from the first low-pass filter 94. The first rubber-bag pressure $P_1$ is quickly increased, by the first rubber-bag pressure control means 120, to a first target value $P_{1M}$ (e.g., about 180 mmHg) sufficiently greater than a systolic blood pressure value $BP_{SYS}$ (e.g., about 120 mmHg) of the subject, and is held at the first target value $P_{1M}$. Concurrently, the pulse-wave detecting device 126 monitors a second rubber-bag pressure $P_2$ of the second rubber bag 64, based on the second rubber-bag pressure signal $SK_2$ supplied from the second low-pass filter 98. The second rubber-bag pressure $P_2$ is quickly increased, by the second rubber-bag pressure control means 122, to a second target value $P_{2M}$ (e.g., about 50 to 60 mmHg) lower than a mean blood pressure value $BP_{MEAN}$ of the subject, and is held at the second target value $P_{2M}$. In this state, a rising point of the second heart sound II (as the first signal) is detected by the phonocardiographic transducer 16, and a notch (as the second signal) of the brachial pulse wave generated in synchronism with the detected second heart sound II is detected by the second pressure sensor 72. After the detection of the second heart sound II and the notch of the brachial pulse wave, the second rubber-bag pressure control means 122 discharges the pressurized air from the second rubber bag 64.

Further, the BP determining device 124 determines a systolic blood pressure value $BP_{SYS}$ and a diastolic blood pressure value $BP_{DIA}$, according to a well known oscillometric method, based on the variation of respective amplitudes of pulses of the pulse wave represented by the first pulse-wave signal $SM_1$ obtained while the first rubber-bag pressure $P_1$ is slowly decreased from the first target value $P_{1M}$, at a rate of about 3 mmHg/sec, by the first rubber-bag pressure control means 120. The systolic and diastolic BP display devices 38, 40 display the determined systolic and diastolic blood pressure values $BP_{SYS}$, $BP_{DIA}$, respectively.

Figure 5A:
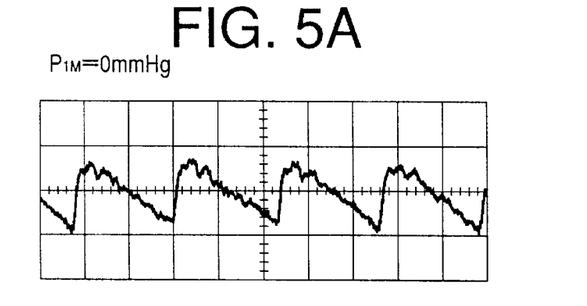
FIGS. 5A, 5B, 5C, and 5D are views showing respective waveforms of a brachial pulse wave detected when a first target value $P_{1M}$ of a first rubber bag is set at 0 mmHg, 60 mmHg, 170 mmHg, and 230 mmHg, respectively.
Figure 5B:
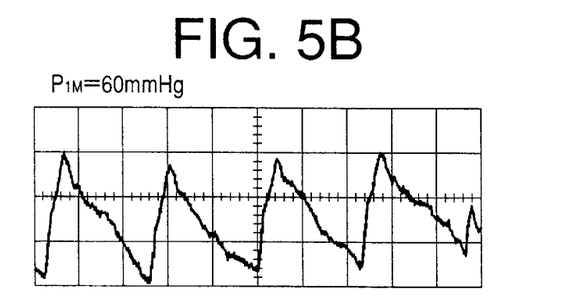
Figure 5C:
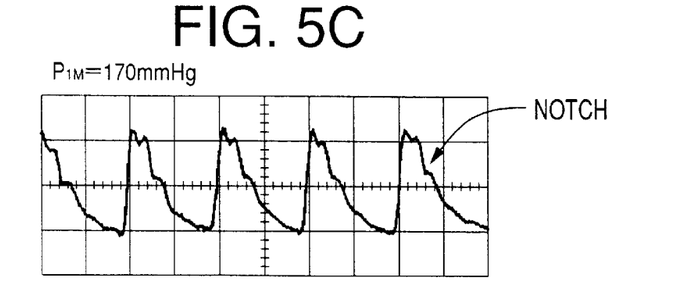
Figure 5D:
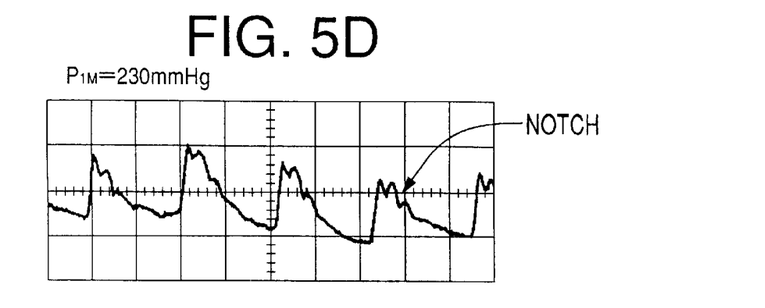

Here, the first target value $P_{1M}$ employed by the pulse wave detecting device 126 is explained. FIGS. 5A, 5B, 5C, and 5D show respective waveforms of the brachial pulse wave (second pulse wave signal $SM_2$) detected by the second pressure sensor 72 and the second low-pass filter 98 when the first target value $P_{1M}$ is set at 0 mmHg, 60 MmHg, 170 mmHg, and 230 mmHg, respectively. As shown in FIGS. 5C and 5D, in the case where the first rubber-bag pressure $P_1$ is greater than the systolic blood pressure value $BP_{SYS}$, a notch of each of successive pulses of the brachial pulse wave is clearly detected. On the other hand, in the case where the first rubber-bag pressure $P_1$ is sufficiently smaller than the systolic blood pressure value $BP_{SYS}$, the notch cannot be detected, as shown in FIGS. 5A and 5B. It is speculated that the reason for this is such that the amplitude of each pulse of the brachial pulse wave detected from the upstream side relative to the first rubber bag 62 with respect to the brachial artery increases when the first rubber bag 62 presses the brachial artery. In other words, since the blood flow in the brachial artery on the downstream side relative to the second rubber bag 64 is limited by the first rubber bag 62, a pulsation generated from the portion of the subject on which the second rubber bag 64 is worn increases. Specifically, in the state in which the first rubber-bag pressure $P_1$ is greater than the systolic blood pressure value $BP_{SYS}$, the blood flow in the brachial artery is completely stopped, whereby a notch of each pulse of the brachial pulse wave can be clearly detected.

Figure 6:
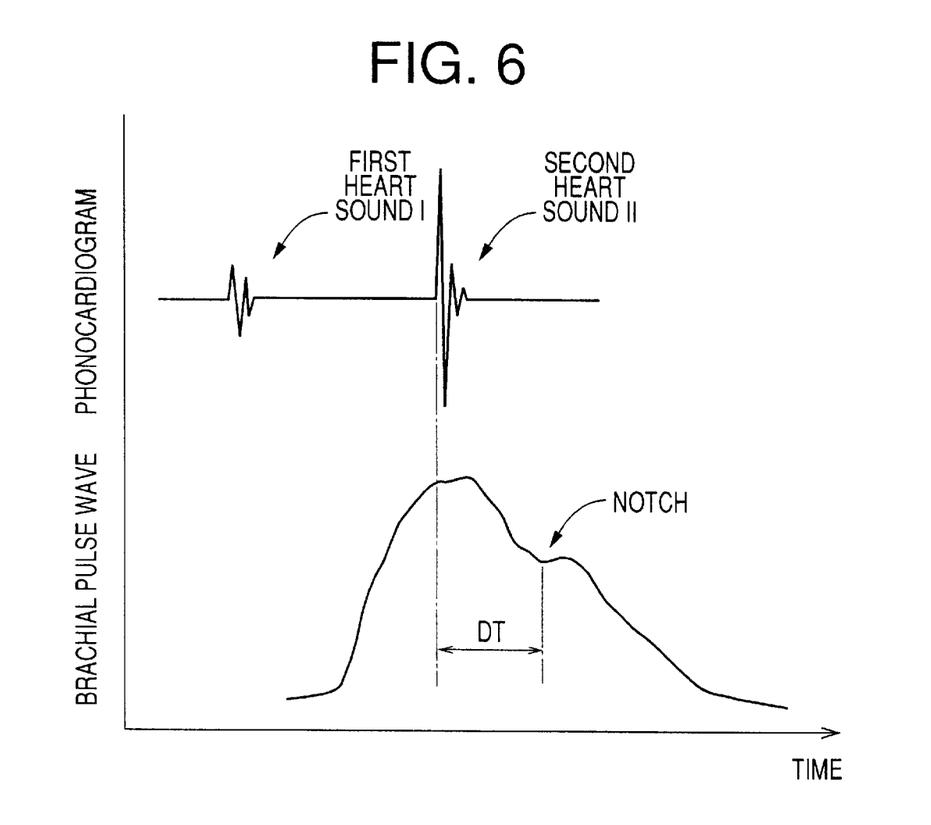
FIG. 6 is a view to show a time difference, DT, determined by a pulse-wave propagation time determining means of FIG. 4.

A pulse-wave propagation time (PWT) determining means 128 determines a time difference DT (sec) (shown in FIG. 6) between a time when the rising point of the second heart sound II is detected by the phonocardiographic transducer 16 and a time when the notch of the brachial pulse wave generated in synchronism with the detected second heart sound II is detected by the second pressure sensor 72 in the state in which the first rubber-bag pressure $P_1$ is held at the first target value $P_{1M}$ and the second rubber-bag pressure $P_2$ is held at the second target value $P_{2M}$.

A pulse-wave propagation velocity (PWV) determining means 130 determines a distance L (m) between the heart of the subject and the portion of the subject on which the second rubber bag 64 is worn, based on the stature of the subject input through the input device 14, according to a predetermined relationship between distance and stature, determines a pulse-wave propagation velocity PWV (m/sec) by dividing the determined distance L by the time difference DT determined by the PWT determining means 128, and displays the determined PWV on the PWV display device 42 of the display panel 36.

Next, there will be described the operation of the arithmetic control circuit 90 of the PWPI obtaining apparatus 10 by reference to the flow chart of FIG. 7.

Figure 7:
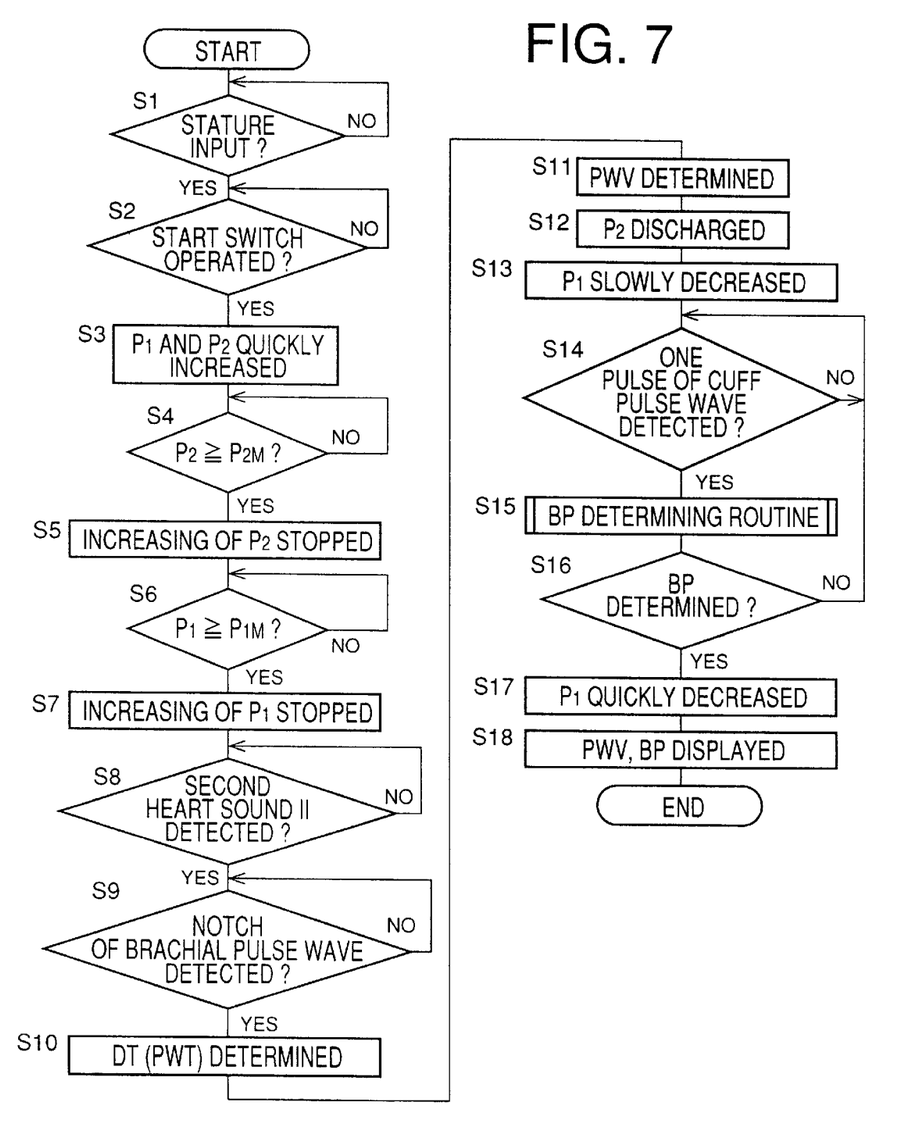
FIG. 7 is a flow chart representing an essential operation of the control circuit of the apparatus of FIG. 1.

At Step S1 of the FIG. 7, the CPU 100 judges whether or not a stature of the subject is input through the input device 14. The CPU 100 waits at Step S1 until the stature of the subject is input by a living subject (e.g., a patient) or an attendant.

If a positive judgment is made at Step S1, the control of the CPU 100 goes to Step S2. At Step S2, the CPU 100 judges whether or not the start switch 30 or 53 has been operated for starting the apparatus 10. To start the operation of the apparatus 10, it is needed to operate the start switch 30, 53 by the attendant or one hand of the subject, in a state in which the other arm of the subject is inserted in the arm receiver 22 and the phonocardiographic transducer 16 is worn on the skin of the chest of the subject with the one hand, the adhesive tape, or the like. Thus, at Step S2, the CPU 100 judges whether or not the start switch 30 or 53 has been operated in a state in which a sensor (not shown) provided on an inner surface of the arm receiver 22 has identified that the upper arm 60 of the subject is inserted in the arm receiver 22 and that the heart-sound signal SH is supplied from the phonocardiographic transducer 16.

If a negative judgment is made at Step S2, the control of the CPU 100 waits at Step S2 until a positive judgment is made at Step S2. If a positive judgment is made at Step S2, the control of the CPU 100 goes to Step S3 to start to quickly increase the first and second rubber-bag pressures $P_1$, $P_2$, by respectively switching the first and second selector valves 68, 74 each to the inflation position, and operating the air pump 80. Step S3 corresponds to the first and second rubber-bag pressure control means 120, 122.

Step S3 is followed by Step S4 to judge whether or not the second rubber-bag pressure $P_2$ is equal to or greater than the second target value $P_{2M}$ (e.g., 50 to 60 mmHg). If a negative judgment is made at Step S4, the CPU 100 repeatedly carries out this step until a positive judgment is made, whereby the first and second rubber-bag pressures $P_1$, $P_2$ continue to increase. If a positive judgment is made at Step S4, the control of the CPU 100 goes to Step S5 to switch the second selector valve 74 to the pressure-hold position, so that the second rubber-bag pressure $P_2$ is held at the second target value $P_{2M}$. Step S4 corresponds to the pulse-wave detecting device 126, and Step S5 corresponds to the second rubber-bag pressure control means 122.

Step S5 is followed by Step S6 to judge whether or not the first rubber-bag pressure $P_1$ is equal to or greater than the first target value $P_{1M}$ (e.g., about 180 mmHg). If a negative judgment is made at Step S6, the CPU 100 repeatedly carries out this step until a positive judgment is made, whereby the first rubber-bag pressure $P_1$ continues to increase. If a positive judgment is made at Step S6, the control of the CPU 100 goes to Step S7. At Step S7, the CPU 100 switches the first selector valve 68 to the pressure-hold position, so that the first rubber-bag pressure $P_1$ is held at the first target value $P_{1M}$. Step S6 corresponds to the pulse-wave detecting device 126, and Step S7 corresponds to the first rubber-bag pressure control means 120.

Step S7 is followed by Steps S8 and S9. At Step S8, the CPU 100 judges whether or not a rising point of the second heart sound II has been detected, based on the heart-sound signals SH successively supplied from the phonocardiographic transducer 16. If a negative judgment is made at Step S8, the CPU 100 repeatedly carries out this step until a positive judgment is made. If a positive judgement is made at Step S8, the control of the CPU 100 goes to Step S9. At Step S9, the CPU 100 judges whether or not a notch of one pulse of the brachial pulse wave has been detected, based on the second pulse-wave signal $SM_2$ supplied from the second band-pass filter 96. If a negative judgement is made at Step S9, the CPU 100 repeatedly carries out this step until a positive judgment is made. Steps S8 and S9 correspond to the pulse-wave detecting device 126.

On the other hand, if a positive judgment is made at Step S9, the control of the CPU 100 goes to Step S10. At Step S10, the CPU 100 determines a time difference, that is, pulse-wave propagation time DT, between a time when the rising point of the second heart sound II is detected at Step S8 and a time when the notch of the brachial pulse wave is detected at Step S9. Step S10 corresponds to the PWT determining means 120. Step S10 is followed by Step S11. At Step S11, the CPU 100 determines a distance L (m) between the heart of the subject and the portion of the subject on which the second rubber bag 64 is worn, based on the stature input at Step S1, according to a predetermined relationship between distance and stature, and determines a pulse-wave propagation velocity PWV by dividing the determined distance L by the pulse-wave propagation time DT determined at Step 10. Step S11 corresponds to the PWV determining means 130.

After the determination of the pulse-wave propagation velocity PWV, the control of the CPU 100 goes to Step S12 to switch the second selector valve 74 to the deflation position, so that the second rubber-bag pressure P2 is decreased and eliminated. Step S12 corresponds to the second rubber-bag pressure control means 122.

Step S12 is followed by Step S13 to switch the first selector valve 68 to the slow-deflation position, so that the first rubber-bag pressure $P_1$ is slowly decreased at a rate of about 3 mmHg/sec. Step S13 corresponds to the first rubber-bag pressure control means 120. Step S13 is followed by Steps S14 to S16. Steps S14 to S16 correspond to the BP determining device 124.

At Step S14, the CPU 100 judges whether or not one pulse of a cuff pulse wave is detected, based on the first pulse-wave signals $SM_1$ successively supplied from the first band-pass filter 88. If a negative judgment is made at Step S14, the CPU 100 waits at Step 14 until a positive judgment is made at Step S14. If a positive judgment is made at Step S14, the control of the CPU 100 goes to Step S15 to carry out a blood-pressure determining routine. In this BP determining routine, a systolic and a diastolic blood pressure value $BP_{SYS}$, $BP_{DIA}$ are determined, according to a well known oscillometric type blood pressure determining algorithm, based on the variation of respective amplitudes of pulses of the cuff pulse wave successively detected at Step S14, while the first rubber-bag pressure $P_1$ is slowly decreased.

Step S15 is followed by Step S16 to judge whether or not the BP determining routine has ended. In short, the CPU 100 judges whether or not the diastolic blood pressure value $BP_{DIA}$ of the subject has been determined. If a negative judgment is made at Step S16, the control of the CPU 100 repeats to Step S14 and the following Steps until a positive judgment is made at Step S16. If a positive judgment is made at Step S16, the control of the CPU 100 goes to Step S17 to switch the first selector valve 68 to the quick-deflation position, so that the first rubber-bag pressure $P_1$ is quickly decreased and eliminated. Step S17 corresponds to the first rubber-bag pressure control means 120.

Step S17 is followed by Step S18. At Step S18, the CPU 100 displays, on the PWV display device 42, the pulse-wave propagation velocity PWV determined at Step S11, and displays, on the systolic and diastolic BP display devices 38, 40, the systolic and diastolic blood pressure values $BP_{SYS}$, $BP_{DIA}$ determined at Step S16, respectively. Thus, the present routine is ended.

In the above described embodiment, the PWT determining means 128 (Step S10) determines, as the pulse-wave propagation time DT, a time difference between the time when the second heart sound II generated in synchronism with the heart beat of the subject is detected by the phonocardiographic transducer 16 and a time when the notch of the brachial pulse wave generated in synchronism with the heart beat is detected by the second rubber bag 64 in the state in which the brachial artery in the upper arm 60 is pressed by the first rubber bag 62. The second rubber bag 64 is worn on the portion of the upper arm 60 being on the upstream side relative to the first rubber bag 62 with respect to the brachial artery and being in proximity to the first rubber bag 62. In the above mentioned state, the notch of the brachial pulse wave is clearly detected, whereby a time when the notch of the brachial pulse wave is detected can be accurately determined. Thus, this apparatus 10 can determine an accurate pulse-wave propagation time DT based on the accurate time when the notch is detected.

In the above described embodiment, the PWPI obtaining apparatus 10 employs, as the pulse-wave detecting device, the brachial pulse-wave detecting device 99 including the second rubber bag 64 worn on the upper arm 60 of the subject for detecting the notch of each pulse of the brachial pulse wave; and, as the pressing device, the first rubber bag 62 worn on the upper arm 60 for determining the blood pressure of the subject. The present apparatus 10 further employs the pressure control device 82 which changes the first rubber-bag pressure $P_1$ and the BP determining device 124 (Steps S14–S16) which determines the blood pressure of the subject based on the signals successively detected while the first rubber-bag pressure $P_1$ is slowly changed by the pressure control device 82. Thus, the present apparatus 10 can determine the blood pressure BP of the subject in addition to the pulse-wave propagation velocity PWV.

In the above described embodiment, the brachial pulse-wave detecting device 99 includes the second rubber bag 64 worn on the portion of the upper arm 60 being on the upstream side relative to the first rubber bag 64 with respect to the brachial artery, and detects the brachial pulse wave based on the variation of the second rubber-bag pressure $P_2$. The first and second rubber bags 62, 64 are accommodated in the outer bag 56 in the state in which the first and second rubber bags are spaced form each other. Thus, since only the outer bag 56 and the phonocardiographic transducer 16 are worn on the subject for determining the pulse-wave propagation velocity PWV, the present apparatus 10 can easily determine the pulse-wave propagation velocity PWV.

In the above described embodiment, the PWT determining means 128 (Step S11) employs the notch of the brachial pulse wave detected in the state in which the first rubber-bag pressure $P_1$ is greater than the systolic blood pressure $BP_{SYS}$ of the subject. In other words, the PWT determining means 128 determines the pulse-wave propagation time DT based the notch of the brachial pulse wave detected from the second rubber bag 64 in the state in which the blood flow in the brachial artery on the downstream side relative to the second rubber bag 64 is completely stopped by the first rubber bag 62. In the state in which the blood flow in the artery on the downstream side relative to the second rubber bag 64 is completely stopped, the amplitude of the brachial pulse wave significantly increases. Therefore, the notch of each pulse of the brachial pulse wave can be accurately detected, whereby the time when the notch is detected can be accurately determined. Thus, the pulse-wave propagation time DT determined based on the accurate time of the notch is detected enjoys high accuracy.

In the above described embodiment, the rising point of the second heart sound II and the notch of the brachial pulse wave are detected for determining the pulse-wave propagation time DT, when the first rubber-bag pressure $P_1$ is increased to the first target value $P_{1M}$ for determining the blood pressure BP of the subject. Thus, the present apparatus 10 can determine the blood pressure BP and pulse-wave propagation time DT of the subject at one time.

While the present invention has been described in its preferred embodiment by reference to the drawings, it is to be understood that the invention may otherwise be embodied.

While in the illustrated embodiment the brachial pulse-wave detecting device 99 worn on the upper arm 60 of the subject is employed as the pulse-wave detecting device for detecting the second signal, it is possible to employ a femoral pulse-wave detecting device worn on a femoral region of the subject for detecting a pulse wave from a femoral artery, or a tibial pulse-wave detecting device worn on an ankle of the subject for detecting a pulse wave from an artery (e.g., a pretibial artery or a posttibial artery) present in the ankle.

In the illustrated embodiment, the second heart sound II generated in synchronism with the heart beat of the subject is employed as the first signal and the notch of the brachial pulse wave detected in synchronism with the heart beat of the subject is employed as the second signal. In short, the first signal is detected on the upstream side relative to the portion of the subject from which the second signal is detected with respect to an artery of the subject. However, the first signal may be detected on a downstream side relative to the portion of the subject from which the second signal is detected. In the latter case, the first signal detecting device is required to be worn on a portion of the subject being on a downstream side relative to the pulse-wave detecting device with respect to another or second artery of the subject because the downstream side relative to the pulse-wave detecting device with respect to the first artery is pressed by the pressing device. For example, in the case where the notch of the brachial pulse wave detected by the brachial pulse-wave detecting device 99 is employed as the second signal and the pressing device is worn on the right upper arm 60 of the subject, the first signal detecting device may be worn on a portion of the left arm of the subject being on a downstream side relative to a portion of the right upper arm on which the brachial pulse-wave detecting device 99 is worn such as a wrist and a finger, or an inferior limb (such as a femoral region or an ankle) of the subject.

While in the illustrated embodiment both the pulse-wave propagation time DT and the blood pressure BP are determined, only the information relating to the propagation velocity of the pulse wave (the pulse-wave propagation time DT and/or the pulse-wave propagation velocity PWV determined based on the time DT) may be obtained.

In the illustrated embodiment, for determining the pulse-wave propagation time DT and the blood pressure BP at one time, the brachial pulse wave is detected in the state in which the first rubber-bag, pressure $P_1$ is equal to or greater than the first target value $P_{1M}$ sufficiently greater than the systolic blood pressure value $BP_{SYS}$. However, in the case where only the information relating to the propagation velocity of the pulse wave such as the pulse-wave propagation time DT is determined, the first rubber-bag pressure $P_1$ may be equal to or slightly greater than the systolic blood pressure value $BP_{SYS}$ of the subject, because the blood flow in the brachial artery is completely stopped with the pressure not smaller than the systolic blood pressure value $BP_{SYS}$. In addition, in the case where the blood flow in the brachial artery is limited to some degree by the first rubber bag 62 worn on the portion of the subject being on the downstream side relative to the second rubber bag 64, the notch of the brachial pulse wave is clearly detected by the second rubber bag 64. Therefore, the second rubber-bag pressure $P_2$ may be set at a pressure value smaller than the systolic blood pressure value $B_{SYS}$, for example, the mean blood pressure value $BP_{MEAM}$ of the subject.

In the illustrated embodiment, the first rubber bag 62 having the predetermined width needed for the blood pressure determining operation is employed as the pressing device. However, in the case where the blood pressure is not determined, the width of the first rubber bag 62 may be greater or smaller than the predetermined width. Additionally, a belt or the like may be employed as the pressing device.

In the illustrated embodiment, for determining the pulse-wave propagation velocity PWV, the stature of the subject is input in advance and the distance L between the heart of the subject and the portion of the subject on which the second rubber bag 64 is worn is determined based on the input stature. However, in the case where the condition of an arterial sclerosis or the effect of a hypotensive drug is monitored, only the timewise change of the pulse-wave propagation velocity PWV may be obtained. Therefore, without inputting the stature of the subject, a predetermined value may be employed as the distance L.

While in the illustrated embodiment the phonocardiographic transducer 16 is employed as the first signal detecting device and the second heart sound II detected by the phonocardiographic transducer 16 is employed as the first signal, a first heart sound I may be employed as the first signal. Further, an electrocardiographic waveform detecting device which detects an electrocardiographic waveform through a plurality of electrodes worn on the subject may be employed as the first signal detecting device, and one of a Q-wave, a R-wave, and a S-wave of the detected electrocardiographic waveform may be employed as the first signal.

It is to be understood that the present invention may be embodied with other changes, modifications, and improvements that may occur to one skilled in the art without departing from the spirit and scope of the invention defined in the appended claims.

What is claimed is:

1. An apparatus for obtaining an information relating to a propagation velocity of a pulse wave which propagates through an artery of a living subject, comprising:

a first signal detecting device which is adapted to be worn on a first portion of the subject and which detects a first signal generated from the first portion in synchronism with a heart beat of the subject;

a pulse-wave detecting device which is adapted to be worn on a second portion of the subject and which detects, as a second signal, a notch of said pulse wave generated from the second portion in synchronism with said heart beat of the subject;

a pressing device which is adapted to be worn on a third portion of the subject to press the third portion, the third portion being on a downstream side relative to the second portion of the subject with respect to said artery and being in proximity to the second portion; and pulse-wave propagation time determining means for determining, as said information, a time difference between a time when said first signal is detected by the first signal detecting device and a time when said notch of the pulse wave is detected by the pulse-wave detecting device in a state in which the third portion of the subject is pressed by the pressing device.

2. An apparatus according to claim 1, wherein said pulse-wave detecting device comprises a brachial pulse-wave detecting device which is adapted to be worn on an upper arm of the subject and which detects a notch of a brachial pulse wave of the subject, and said pressing device comprises a first rubber bag which is adapted to be worn on the upper arm of the subject for determining a blood pressure of the subject, the apparatus further comprising:

a pressure control device which changes a pressing pressure of the first rubber bag; and a blood pressure determining device which determines said blood pressure of the subject, based on signals successively detected while the pressing pressure of the first rubber bag is changed by the pressure control device.

3. An apparatus according to claim 2, wherein said brachial pulse-wave detecting device comprises a second rubber bag for detecting said brachial pulse wave of the subject, the second rubber bag being adapted to be worn on an upstream side relative to a portion of the upper arm on which the first rubber bag is worn, the apparatus further comprising an outer bag in which the first and second rubber bags are accommodated in a state in which the first and second rubber bags are spaced from each other.

4. An apparatus according to claim 2, wherein said pulse-wave propagation time determining means determines said time difference between said time when said first signal is detected and said time when said notch of the brachial pulse wave is detected by the brachial pulse-wave detecting device in said state in which the upper arm is pressed by said first rubber bag with a pressing pressure greater than a reference value which is greater than a systolic blood pressure of the subject, and wherein said blood pressure determining device determines, after detection of the first signal and the notch of the brachial pulse wave, said blood pressure of the subject, based on the signals successively detected while the pressing pressure of the first rubber bag is decreased by the pressure control device.

5. An apparatus according to claim 1, wherein said pulse-wave propagation time determining means determines said time difference between said time when said first signal is detected and said time when said notch of the pulse wave is detected in said state in which said third portion is pressed by said pressing device with a pressing pressure greater than a systolic blood pressure of the subject.

6. An apparatus according to claim 1, wherein said first signal detecting device comprises a phonocardiographic transducer which detects, as the first signal, one of a first and a second heart sound of the subject.

7. An apparatus according to claim 6, wherein said phonocardiographic transducer has a switch which is manually operable for starting the apparatus.

8. An apparatus according to claim 1, further comprising a pulse-wave propagation velocity determining means for determining said propagation velocity of the pulse wave, by dividing a distance between a heart of the subject and the second portion of the subject by the time difference determined by said pulse-wave propagation time determining means.

9. An apparatus according to claim 8, further comprising an input device which is operable for inputting a stature of the subject, wherein said pulse-wave propagation velocity determining means comprises means for determining said distance between the heart of the subject and the second portion of the subject, based on said stature of the subject input through the input device, according to a predetermined relationship between distance and stature; and means for determining said propagation velocity of the pulse wave by dividing the determined distance by the time difference determined by said pulse-wave propagation time determining means.

* * * * *